US007794399B2

(12) United States Patent
Singh

(10) Patent No.: US 7,794,399 B2
(45) Date of Patent: Sep. 14, 2010

(54) SYSTEM AND METHOD FOR THREE-DIMENSIONAL AIRWAY RECONSTRUCTION, ASSESSMENT AND ANALYSIS

(75) Inventor: Gurdev Dave Singh, San Juan, PR (US)

(73) Assignees: Tamir Cohen, N. Miami Beach, FL (US); Ran Ben-David, N. Miami Beach, FL (US)

( * ) Notice: Subject to any disclaimer, the term of this patent is extended or adjusted under 35 U.S.C. 154(b) by 1270 days.

(21) Appl. No.: 11/338,554

(22) Filed: Jan. 24, 2006

(65) Prior Publication Data

US 2007/0173724 A1    Jul. 26, 2007

(51) Int. Cl.
 A61B 5/08    (2006.01)
 A61B 8/00    (2006.01)
(52) U.S. Cl. .................................. 600/443; 600/529
(58) Field of Classification Search ............... 600/529, 600/437, 443
See application file for complete search history.

(56) References Cited

U.S. PATENT DOCUMENTS

| 5,316,002 | A | 5/1994 | Jackson et al. |
| 5,666,960 | A | 9/1997 | Fredberg et al. |
| 5,699,809 | A | 12/1997 | Combs et al. |
| 5,746,699 | A | 5/1998 | Fredberg et al. |
| 5,823,965 | A | 10/1998 | Rasmussen |
| 5,868,682 | A | 2/1999 | Combs et al. |
| 6,379,311 | B1 * | 4/2002 | Gaumond et al. ........... 600/529 |
| 6,491,641 | B1 | 12/2002 | Rasmussen |
| 6,950,689 | B1 * | 9/2005 | Willis et al. ................. 600/407 |
| 2003/0052875 | A1 * | 3/2003 | Salomie ..................... 345/419 |
| 2005/0019732 | A1 * | 1/2005 | Kaufmann et al. .......... 433/213 |
| 2005/0119586 | A1 | 6/2005 | Coyle et al. |

OTHER PUBLICATIONS

Ahmad et al., Evaluation with acoustic rhinometry of patients undergoing sinonasal surgery, Med J Malaysia, Dec. 2003; 58(5), pp. 723-728, Abstract.
Cakmak et al., Value of acoustic rhinometry for measuring nasal valve area, Laryngoscope, Feb. 2003; 113(2), pp. 295-302, Abstract.
Capone et al., The effect of rhytidectomy on the nasal valve, Arch Facial Plast Surg.,Jan.-Feb. 2005; 7(1), pp. 45-50, Abstract.

(Continued)

Primary Examiner—Patricia C Mallari
(74) Attorney, Agent, or Firm—Hunton & Williams LLP

(57) ABSTRACT

This invention relates to a system and method for three-dimensional airway reconstruction, assessment and analysis. Specifically, the invention relates to a system and method for acquiring one- and two-dimensional data regarding a cavity, such as an esophagus or an airway, and manipulating that data to reconstruct a three-dimensional geometrical object representing that cavity. Suitable data collection methods include, but are not limited to, non-ionizing, non-invasive protocols including acoustic reflectometry, such as that performed by a DOS®- or Windows®-based pharyngometer or rhinometer. The resulting three-dimensional geometric object of the subject cavity can be used to diagnose cavity morphology/obstruction, aid in management and treatment of the obstruction, evaluate efficacy of management and treatment of the obstruction and also provide information for use in outcome analysis and forensic and medico-legal evaluation of diagnosis and treatment of cavity obstruction/stenosis.

9 Claims, 6 Drawing Sheets

OTHER PUBLICATIONS

Carlini et al., Modified method of acoustic rhinometry, Acta Otolaryngol. Apr. 2002; 122(3), pp. 298-301, Abstract.

Cheng et al., Characterization of nasal spray pumps and deposition pattern in a replica of the human nasal airway, J Aerosol Med. 2001 Summer; 14(2), pp. 267-280, Abstract.

De Moura et al., Rapid maxillary expansion and nasal patency in children with Down syndrome, Rhinology, Jun. 2005; 43(2), pp. 138-142, Abstract.

Djupesland et al., Accuracy of acoustic rhinometry, Rhinology. Mar. 2001;39(1), pp. 23-27, Abstract.

Dreher et al., Correlation between otorhinolaryngologic evaluation and severity of obstructive sleep apnea syndrome in snorers, Arch Otolaryngol Head Neck Surg. Feb. 2005; 131(2), pp. 95-98, Abstract.

Faber et al., Available techniques for objective assessment of upper airway narrowing in snoring and sleep apnea, Sleep Breath. Jun. 2003;7(2), pp. 77-86, Abstract.

Filho et al., A comparison of nasopharyngeal endoscopy and lateral cephalometric radiography in the diagnosis of nasopharyngeal airway obstruction, Am J Orthod Dentofacial Orthop. Oct. 2001; 120(4), pp. 348-352, Abstract.

Gosepath et al., The use of acoustic rhinometry in predicting outcomes after sinonasal surgery, Am J Rhinol. Mar.-Apr. 2000; 14(2), pp. 97-100, Abstract.

Huang et al., A new nasal acoustic reflection technique to estimate pharyngeal cross-sectional area during sleep, J Appl Physiol. Apr. 2000;88(4), pp. 1457-1466, Abstract.

Huang et al., Evaluation of nasal cavity by acoustic rhinometry in Chinese, Malay and Indian ethnic groups, Acta Otolaryngol. Oct. 2001;121(7), pp. 844-848, Abstract.

Jurlina et al., Correlation between the minimal cross-sectional area of the nasal cavity and body surface area: preliminary results in normal patients, Am J Rhinol. Jul.-Aug. 2002;16(4), pp. 209-213, Abstract.

Kalmovich et al., Endonasal geometry changes in elderly people: acoustic rhinometry measurements, J Gerontol A Biol Sci Med Sci. Mar. 2005;60(3), pp. 396-398, Abstract.

Lal et al., Acoustic rhinometry and its uses in rhinology and diagnosis of nasal obstruction, Facial Plast Surg Clin North Am. Nov. 2004;12(4), pp. 397-405, Abstract.

Mamikoglu et al., Acoustic rhinometry and computed tomography scans for the diagnosis of nasal septal deviation, with clinical correlation, Otolaryngol Head Neck Surg. Jul. 2000;123(1 Pt 1), pp. 61-68, Abstract.

Modrzynski et al., Additional diagnostic methods for recording of adenoid hypertrophy in children with allergic rhinitis, Article in Polish, Przegl Lek. 2004;61(2), pp. 74-77, Abstract.

Modrzynski et al., Acoustic rhinometry in the assessment of adenoid hypertrophy in allergic children, Med Sci Monit. Jul. 2004;10(7):CR431-8. Epub Jun. 29, 2004, Abstract.

Morris et al., Nasal obstruction and sleep-disordered breathing: a study using acoustic rhinometry, Am J Rhinol. Jan.-Feb. 2005;19(1), pp. 33-39, Abstract.

Niikuni et al., The relationship between tongue-base position and craniofacial morphology in preschool children, J Clin Pediatr Dent. 2004 Winter;28(2), pp. 131-134, Abstract.

Nuhoglu et al., Does recurrent sinusitis lead to a sinusitis remodeling of the upper airways in asthmatic children with chronic rhinitis?, J Investig Allergol Clin Immunol. 2003;13(2), pp. 99-102, Abstract.

Numminen et al., Correlation between rhinometric measurement methods in healthy young adults, Am J Rhinol. Jul.-Aug. 2002;16(4), pp. 203-208, Abstract.

Numminen et al., Reliability of acoustic rhinometry, Respir Med. Apr. 2003;97(4), pp. 421-427, Abstract.

Nurminen et al., Modelling the reproducibility of acoustic rhinometry, Stat Med. May 15, 2000;19(9), pp. 1179-1189, Abstract.

Roberts et al., How do you size a nasopharyngeal airway, Resuscitation. Jan. 2003;56(1), pp. 19-23, Abstract.

Terheyden et al., Acoustic rhinometry: validation by three-dimensionally reconstructed computer tomographic scans, J Appl Physiol. Sep. 2000;89(3), pp. 1013-1021, Abstract.

Woodson, Expiratory pharyngeal airway obstruction during sleep: a multiple element model, Laryngoscope. Sep. 2003;113(9), pp. 1450-1459, Abstract.

Wong et al., Craniofacial morphology, head posture, and nasal respiratory resistance in obstructive sleep apnoea: an inter-ethnic comparison, Eur J Orthod. Feb. 2005;27(1), pp. 91-97, Abstract.

Yang et al., Acoustic rhinometry measurement from the patients with deviation of nasal septum, Article in Chinese, Lin Chuang Er Bi Yan Hou Ke Za Zhi. Apr. 2004;18(4), pp. 225-226, Abstract.

Zambetti et al., Study and application of a mathematical model for the provisional assessment of areas and nasal resistance, obtained using acoustic rhinometry and active anterior rhinomanometry, Clin Otolaryngol Allied Sci. Aug. 2001;26(4), pp. 286-93, Abstract.

Zambetti et al., Assessment of Cottle's areas through the application of a mathematical model deriving from acoustic rhinometry and rhinomanometric data, Clin Otolaryngol. Apr. 2005;30(2), pp. 128-34, Abstract.

Zheng et al., Nasal cavity volume and nasopharyngeal cavity volume in adults measured by acoustic rhinometry, Article in Chinese, Lin Chuang Er Bi Yan Hou Ke Za Zhi. Nov. 2000;14(11), pp. 494-495, Abstract.

Aldinucci et al., Effects of Dietary Yoghurt on Immunological and Clinical Parameters of Rhinopathic Patients, Abstract, European Journal of Clinical Nutrition, (2002) 56, 1156-1161, doi:10.1038/sj.ejcn.1601465.

Barclay and Lie, Atomized Nasal Douche May be Better Than Lavage for Acute Viral Rhinitis, Medscape Medical News, Relase date Sep. 22, 2005.

Brugel-Ribere et al., Segmental Analysis of Nasal Cavity Compliance by Acoustic Rhinometry, J Appl Physiol 93:304-310, 2002, First published Mar. 22, 2002; doi: 10.1152/japplphysiol.00085.2002; J Appl Physiol vol. 93, Jul. 2002, www.jap.org, pp. 304-310.

Cakmak et al., Effects of Paranasal Sinus Ostia and Volume on Acoustic Rhinometry Measurements: A Model Study, J Appl Physiol 94:1527-1535, 2003, First published Dec. 13, 2002; doi: 10.1152/japplphysiol.01032.2002.

Cankurtaran et al., Effects of the Nasal Valve on Acoustic Rhinometry Measurements: A Model Study, J Appl Physiol 94:2166-2172, 2003, First published Feb. 14, 2003; doi: 10.1152/japplphysiol.01146.2002.

Casadevall et al., Intranasal Challenge With Aspirin in the Diagnosis of Aspirin Intolerant Asthma: Evaluation of Nasal Response by Acoustic Rhinometry, Thorax 2000; 55; 921-924, doi: 10.1136/thorax.55.11.921, thorax.bmjjournals.com.

Celik et al., Acoustic Rhinometry Measurements in Stepped-Tube Models of the Nasal Cavity, Abstract, 2004 Phys. Med. Biol. 49 371-386 doi: 10.1088/0031-9155/49/3/002, Print Publication: Issue 3 (Feb. 7, 2004).

Dastidar et al., Semi-Automatic Segmentation of Computed Tomographic Images in Volumetric Estimation of Nasal Airway, Abstract, European Archives of Oto-Rhino-Laryngology (Eur. arch. oto-rhino-laryngol.) ISSN 0937-4477, Source: 1999, vol. 256, n° 4, pp. 192-198 (13 ref.).

Ellegård et al., Ige-Mediated Reactions and Hyperreactivity in Pregnancy Rhinitis, Arch Otolaryngol Head Neck Surg/vol. 125, Oct. 1999, 5 pages.

Fodil et al., Inspiratory Flow in the Nose: A Model Coupling Flow and Vasoerectile Tissue Distensibility, J Appl Physiol 98:288-295, 2005, First published Aug. 27, 2004; doi: 10.1152/japplphysiol.00625.2004.

Giger et al., Comparison of Once-Versus Twice-Daily Use of Beclomethasone Dipropionate Aqueous Nasal Spray in the Treatment of Allergic and Non-Allergic Chronic Rhinosinusitis, Abstract, European Archives of Oto-Rhino-Laryngology (Eur. arch. oto-rhinolaryngol.) ISSN 0937-4477, Source: 2003, vol. 260, n° 3, pp. 135-140.

Gotlib, et al., Bilateral Nasal Allergen Provocation Monitored with Acoustic Rhinometry. Assessment of Both Nasal Passages and the Side Reacting With Greater Congestion: Relation to the Nasal Cycle, Abstract, Clinical and Experimental Allergy (Clin. Exp. Allergy) ISSN 0954-7894, Source: 2005, vol. 35, n° 3, pp. 313-318.

Graf et al., Ten Days' Use of Oxymetazoline Nasal Spray With or Without Benzalkonium Chloride in Patients with Vasomotor Rhinitis, Arch Otolaryngol Head Neck Surg/vol. 125, Oct. 1999, pp. 1128-1132, www.archoto.com.

Grützenmacher et al., The Combination of Acoustic Rhinometry, Rhinoresistometry and Flow Simulation in Noses before and after Turbinate Surgery: A Model Study, Abstract, Department of Otorhinolaryngology, Head and Neck Surgery Ernst-Moritz-Arndt University Greifswald, Greifswald, Germany, ORL 2003; 65:341-347 (DOI: 10.1159/000076052), Oct. 30, 2003.

Hellgren et al., Nasal Symptoms Among Workers Exposed to Soft Paper Dust, Abstract, International Archives of Occupational and Environmental Health (Int. Arch. Occup. Environ. Health) ISSN: 0340-0131, CODEN IAEHDW, 2001, vol. 74, n°2, pp. 129-132.

Hellgren et al., Increased Nasal Mucosal Swelling in Subjects With Asthma, Abstract, Clinical and Experimental Allergy (Clin. exp. allergy) ISSN 0954-7894, 2002, vol. 32, n°1, pp. 64-69.

Hilberg, Objective Measurement of Nasal Airway Dimensions Using Acoustic Rhinometry: Methodological and Clinical Aspects, ALLERGY 2002: 57 (Suppl. 70): 5-39, ISSN 0108-1675, pp. 5-39.

Hirschberg, Rhinomanometry: An Update, Semmelweis University, Faculty of Medicine, Department of ORL and HNS, Budapest, Hungary, hirschberg@fulo.sote.hu; PMID: 12232472 [PubMed—indexed for MEDLINE].

Houser et al., Acoustic Rhinometry Findings in Patients With Mild Sleep Apnea, Abstract, Otolaryngology—Head and Neck Surgery (Otolaryngol. Head Neck Surg.) ISSN 0194-5998, CODEN OHNSDL, 2002, vol. 126, n°5, pp. 475-480.

Kaise et al., Involvement of Neuropeptides in the Allergic Nasal Obstruction in Guinea Pigs, Jpn. J. Pharmacol. 86, 196-2002 (2001).

Koss et al., Measurement of Nasal Patency in Anesthetized and Conscious Dogs, J Appl Physiol 92:617-621, 2002, First published Oct. 5, 2001; doi: 10.1152/japplphysiol.00891.2001.

Moberg et al., Smaller Nasal Volumes as Stigmata of Aberrant Neurodevelopment in Schizophrenia, AM J Psychiatry 2004; 161:2314-2316.

Mösges et al., Topical Treatment of Rhinosinusitis With Fusafungine Nasal Spray: A Double-Blind, Placebo-Controlled, Parallel-Group Study in 20 Patients, Abstract, Arzneimittel-Forschung (Arzneim.-Forsch) ISSN 0004-4172 CODEN ARZNAD, 2002, vol. 52, n°12, pp. 877-883.

Nurminen et al., Modelling the Reproducibility of Acoustic Rhinometry, Abstract, Statistics in Medicine (Stat. med.) ISSN 0277-6715, 2000, vol. 19, n°9, pp. 1179-1189.

Opiekum et al., Assessment of Ocular and Nasal Irritation in Asthmatics Resulting From Fragrance Exposure, Abstract, Clinical and Experimental Allergy (Clin. Exp. Allergy) ISSN 0954-7894, 2003, vol. 33, n°9, pp. 1256-1265.

Peltonen et al., Effect of the Nasal Strip and Dilator on Nasal Breathing: A Study in Healthy Subjects, Abstract, Rhinology ISSN 0300-0729, 2004, vol. 42, n°3, pp. 122-125.

Phipatanakul et al., A Randomized, Double-Blind, Placebo-Controlled Trial of the Effect of Zafirlukast on Upper and Lower Respiratory Responses to Cat Challenge, Abstract, The Journal of Allergy and Clinical Immunology (J. Allergy Clin. Immunol.) ISSN 0091-6749 CODEN JACIBY, 2000, vol. 105, n°4, pp. 704-710.

Raphael, David T., M.D., Ph.D., "Acoustic Reflectometry Profiles of Endotracheal and Esophageal Intubation," Anesthesiology. 92(5): 1293-1299, May 2000.

Rhinomanometry and Acoustic Rhinometry, Clinical Policy Bulletins, No. 0700, Reviewed: Dec. 13, 2005.

Schlünssen et al., Nasal Patency is Related to Dust Exposure in Woodworkers, Occup. Environ. Med. 2002; 59; 23-29; doi: 10.1136/oem.59.1.23.

Shemen, Larry, M.D., F.R.C.S., F.A.C.S. and Richard Hamburg, M.D., F.A.C.S., "Preoperative and Postoperative Nasal Septal Surgery Assessment With Acoustic Rhinometry," presented at the Annual Meeting of the American Academy of Otolaryngology-Head and Neck Surgery, Washington, DC, Sep. 29-Oct. 2, 1996, p. 338.

Straszek et al., Acoustic Rhinometry in Dog and Cat Compared With a Fluid-Displacement Method and Magnetic Resonance Imaging, J Appl Physiol 95:635-642, 2003. First published Apr. 18, 2003, doi: 10.1152/japplphysiol.01105.2002.

Straszek et al., Nasal Cavity Dimensions in Guinea Pig and Rat Measured by Acoustic Rhinometry and Fluid-Displacement Method, J Appl Physiol 96:2109-2114, 2004. First published Feb. 13, 2004; doi: 10.1152/japplphysiol.00540.2003.

Swierczynska et al., Nasal Versus Bronchial and Nasal Response to Oral Aspirin Challenge: Clinical and Biochemical Differences Between Patients With Aspirin-Induced Asthma/Rhinitis, Abstract, The Journal of Allergy and Clinical Immunology (J. Allergy Clin. Immunol.) ISSN 0091-6749, CODEN JACIBY, 2003, vol. 112, n°5, pp. 995-1001.

Tarhan et al., Acoustic Rhinometry in Humans: Accuracy of Nasal Passage Area Estimates, and Ability to Quantify Paranasal Sinus Volume and Ostium Size, J Appl Physiol 99: 616-623, 2005. First published Mar. 31, 2005; doi: 10.1152/japplphysiol.00106.2005.

Terheyden et al., Acoustic Rhinometry: Validation by Three-Dimensionally Reconstructed Computer Tomographic Scans, J Appl Physiol 89:1013-1021, 2000.

Terrien et al., Comparison of the Effects of Terfenadine With Fexofenadine on Nasal Provocation Tests With Allergen, Abstract, The Journal of Allergy and Clinical Immunology (J. allergy clin. immunol.) ISSN 0091-6749, CODEN JACIBY, 1999, vol. 103, n°6, pp. 1025-1030.

Tiniakov et al., Canine Model of Nasal Congestion and Allergic Rhinitis, J Appl Physiol 94: 1821-1828, 2003. First published Jan. 24, 2003; doi: 10.1152/japplphysiol.00930.2002.

Ulvestad et al., Gas and Dust Exposure in Underground Construction is Associated With Signs of Airway Inflammation, Eur Respir J 2001; 17: 416-421.

Watanabe et al., Oxymetazoline Nasal Spray Three Times Daily for Four Weeks in Normal Subjects is Not Associated With Rebound Congestion or Tachyphylaxis, Abstract, Rhinology (Rhinology) ISSN 0300-0729, 2003, vol. 41, n°3, pp. 167-174.

Wieslander et al., Nasal and Ocular Symptoms, Tear Film Stability and Biomarkers in Nasal Lavage, in Relation to Building-Dampness and Building Design in Hospitals, Abstract, International Archives of Occupational and Environmental Health (Int. Arch. Occup. Environ. Health) ISSN 0340-0131, CODEN IAEHDW, 1999, vol. 72, n°7, pp. 451-461.

Wieslander et al., Inflammation Markers in Nasal Lavage, and Nasal Symptoms in Relation to Relocation to a Newly Painted Building: A Longitudinal Study, Abstract, International Archives of Occupational and Environmental Health (Int. Arch. Occup. Environ. Health) ISSN 0340-0131, CODEN IAEHDW, 1999, vol. 72, n°8, pp. 507-515.

Wieslander et al., Changes in the Ocular and Nasal Signs and Symptoms of Aircrews in Relation to the Ban on Smoking on Intercontinental Flights, Abstract, Scandinavian Journal of Work, Environment & Health (Scand. J. Work, Environ. & Health) ISSN 0355-3140, 2000, vol. 26, n°6, pp. 514-522.

Wieslander et al., Experimental Exposure to Propylene Glycol Mist in Aviation Emergency Training: Acute Ocular and Respiratory Effects, Occup. Environ. Med. 2001; 58; 649-655; doi: 10.1136/oem.58.10.649.

Wiesmüller et al., Value of Acoustic Rhinometry in Environmental Medicine, Abstract, International Journal of Hygiene and Environmental Health (Int. J. Environ. Health) ISSN 1438-4639, 2000, vol. 203, n°1, pp. 55-64.

Wiesmüller et al., Nasal Function in Self-Reported Chemically Intolerant Individuals, Archives of Environmental Health, May-Jun. 2002.

Wilson et al., Effects of Monotherapy With Intra-Nasal Corticosteroid or Combined Oral Histamine and Leukotriene Receptor Antagonists in Seasonal Allergic Rhinitis, Abstract, Clinical and Experimental Allergy (Clin. exp. allergy) ISSN 0954-7894, 2001, vol. 31, n°1, pp. 155-167.

Wilson et al., An Evaluation of Short-Term Corticosteroid Response in Perennial Allergic Rhinitis Using Histamine and Adenosine Monophosphate Nasal Challenge, Abstract, British Journal of Clinical Pharmacology (Br. j. clin. pharmacol.) ISSN 0306-5251 CODEN BCPHBM, 2003, vol. 55, n°4, pp. 354-359.

International Search Report mailed Sep. 26, 2007.

Ahman et al., Nasal Symptoms and Pathophysiology in Farmers, Department of Occupational Health, Karolinska Hospital, Stockholm, Sweden, mats.ahman@smd.sll.se; PMID: 11401020 [PubMed—indexed for MEDLINE], May 2001, Abstract only.

Ahman et al., Nasal Histamine Reactivity in Woodwork Teachers, Department of Occupational Health, Stockholm, Sweden, mats.ahman@smd.sll.se; PMID: 11072656 [PubMed—indexed for MEDLINE], Sep. 2000, Abstract only.

Baraniuk et al., Hypertonic Saline Nasal Provocation and Acoustic Rhinometry, TubMed, Apr. 2002, Abstract only.

Bellussi et al., A New Method for Endoscopic Evaluation in Rhinology: videocapture; PMID: 10780042 [PubMed—indexed for MEDLINE], Mar. 2000, Abstract only.

Bickford et al., The Nasal Airways Response in Normal Subjects to Oxymetazonline Spray: Randomized Double-Blind Placebo-Controlled Trial, Department of Clinical and Experimental Pharmacology, University of Adelaide, South Australia, 5005, Australia; PMID: 10383560 [Pub-Med—indexed for MEDLINE], Jul. 1999, Abstract only.

Cakmak et al., Accuracy of Acoustic Rhinometry Measurements, Otorhinolaryngology Department, Baskent University Faculty of Medicine, Adana Dr. Turgut Noyan Hospital, Adana, Turkey, ozcakmak@hotmail.com; PMID: 11359125 [PubMed—indexed for MEDLINE], Apr. 2000, Abstract only.

Can et al., Acoustic Rhinometry in the Objective Evaluation of Childhood Septoplasties, Ministry of Health Ankara Education and Research Hospital, ENT Clinic, Turkey, ilknurbirol@hotmail.com, Apr. 2005, Abstract only.

Cho et al., Size Assessment of Adenoid and Nasopharyngeal Airway by Acoustic Rhinometry in Children, Department of Otolaryngology-Head and Neck Surgery, College of Medicine, Catholic University of Korea, Seoul, Korea, entcho@cmc.cuk.ac.kr; PMID: 10664704 [PubMed—indexed for MEDLINE], Oct. 1999, Abstract only.

Corey et al., Anatomic Correlates of Acoustic Rhinometry As Measured by Rigid Nasal Endoscopy, Section of Otolaryngology-Head and Neck Surgery, University of Chicago, IL 60637, US; PMID: 10547472 [PubMed—indexed for MEDLINE], Nov. 1999, Abstract only.

Deruaz et al., Levocetirizine Better Protects Than Desloratadine in a Nasal Provocation With Allergen, Division of Allergy and Immunology, Centre Hospitalier Universitaire Vaudois, Rue du Bugnon, 1011 Lausanne, Switzerland, Apr. 2004, Abstract only.

Djupesland et al., Acoustic Rhinometry in Infants and Children, Department of Otorthinolaryngology, Ulleval University Hospital, 0407 Oslo, Norway, per.djupesland@ioks.uio.no; PMID: 11225290 [PubMed—indexed for MEDLINE], Dec. 2000, Abstract only.

Djupesland et al., Technical Abilities and Limitations or Acoustic Rhinometry Optimised for Infants, Department of Otorhinolaryngology, Ullevaal University Hospital Oslo, Norway; PMID: 9830673 [PubMed—indexed for MEDLINE], Sep. 1998, Abstract only.

Elbrond et al., Acoustic Rhinometry, Used as a Method to Demonstrate Changes in the Volume of the Nasopharynx After Adenoidectomy, ENT-Department, University Hospital of Aarhus, Denmark; PMID: 2032366 [PubMed—Indexed for MEDLINE], Feb. 1991.

Elbrond et al., Acoustic Rhinometry, Used as a Method to Monitor the Effect of Intramuscular Injection of Steroid in the Treatment of Nasal Polyps, ENT-Department, University Hospital of Aarhus, Denmark; PMID: 2019801 [PubMed—Indexed for MEDLINE], Mar. 1991, Abstract only.

Ganslmayer et al., Evaluation of Acoustic Rhinometry in a Nasal Provocation Test With Allergen, Division of Immunology and Allergy, Centre Hospitalier Universitaire Vaudois, Lausanne, Switzerland; PMID: 10505461 [PubMed—indexed for MEDLINE], Sep. 1999, Abstract only.

Giger et al., Correlation Between Objective Criteria and Subjective Evaluation of Symptoms in Chronic Rhinosinusitis, Article in French, Unite de rhinologie/Clinique et policlinique d'oto-rhino-laryngologie et de chirurgie cervico-faciale, Hopitaux Universitaires de Geneve; PMID: 10780087 [PubMed—indexed for MEDLINE], (2000), Abstract only.

Grymer, Clinical Applications of Acoustic Rhinometry, ENT-Department, University Hospital, Aarhus, Denmark; PMID: 11225288 [PubMed—indexed for MEDLINE], Dec. 2000, Abstract only.

Grymer et al., Septoplasty and Compensatory Inferior Turbinate Hypertrophy: A Randomized Study Evaluated by Acoustic Rhinometry, Abstract, Univ. Hosp., ENT dep., Aarhus, Denmark, The Journal of Laryngology and Otology (J. Laryngol. Otol.) ISSN 0022-2151, CODEN JLOTAX, 1993, vol. 107, n°5, pp. 413-417, May 1993, Abstract only.

Grymer et al., Acoustic Rhinometry: Values From Adults With Subjective Normal Nasal Patency, ENT-department, University Hospital Aarhus, Denmark; PMID: 1710069 [PubMed—indexed for MEDLINE], Mar. 1991, Abstract only.

Haeggstrom et al., Nasal Mucosal Swelling and Reactivity During a Menstrual Cycle, Department of Otolaryngology, Soder Hospital, Karolinska Institute, Stockholm, Sweden; PMID: 10654316 [PubMed—indexed for MEDLINE], Jan./Feb. 2000, Abstract only.

Harar et al., Improving the Reproductibility of Acoustic Rhinometry in the Assessment of Nasal Function, Department of Otolaryngology—Head and Neck Surgery, Royal Hospitals Trust, London, UK; PMID: 11891393 [PubMed—indexed for MEDLINE], Jan./Feb. 2002, Abstract only.

Heldal et al., Upper Airway Inflammation in Waste Handlers Exposed to Bioaerosols, National Institute of Occupational Health, PO Box 8149, Dep., 0033 Oslo, Norway; kari.heldal@stami.no, Jun. 2003, Abstract only.

Hierl et al., Impact of Short-Time Nasal Intubation on Postoperative Respiration, Department of Oral and Maxillofacial Plastic Surgery, University of Leipzig, Germany, hiet@medizin.uni-leipzig.de; PMID: 10953846 [PubMed—indexed for MEDLINE] Jun. 2000, Abstract only.

Hilberg et al., Acoustic Rhinometry: Evaluation of Nasal Cavity Geometry by Acoustic Reflection, Institute of Environmental and Occupational Medicine, University of Aarhus, Denmark; PMID: 2917933 [PubMed—indexed for MEDLINE], Jan. 1989, Abstract only.

Hilberg et al., Turbinate Hypertrophy. Evaluation of the Nasal Cavity by Acoustic Rhinometry, Institute of Environmental and Occupational Medicine, University of Aarhus, Denmark; PMID: 2306345 [PubMed—indexed for MEDLINE], Mar. 1990, Abstract only.

Hilberg et al., Acoustic Rhinometry: Recommendations for Technical Specifications and Standard Operating Procedures, Institute of Environmental and Occupational Medicine, University of Aarhus, Denmark; PMID: 11225287 [PubMed—indexed for MEDLINE], Dec. 2000, Abstract only.

Ho et al., Measurement of Nasal Geometry by Acoustic Rhinometry in Normal-Breathing Asian Children, Division of Otorhinolaryngology, University of Hong Kong, Queen Mary Hospital, Hong Kong; PMID: 10461262 [PubMed—indexed for MEDLINE], Aug. 1999, Abstract only.

Kamal, Ibrahim M.D., Brigadier General, "Normal Standard Curve for Acoustic Pharyngometry," available from the ENT Department, Police Authority Hospital, 26 Makram Oubaid Street, Nasr City, Egypt, PubMed, Mar. 2001, Abstract only.

Kamami et al., Laser-Assisted Outpatient Septoplasty: Results in 703 Patients, Saint-Cloud Hospital, Paris, France; PMID: 10699825 [PubMed—indexed for MEDLINE] , Mar. 2000, Abstract only.

Kemker et al., Effect of Nasal Surgery on the Nasal Cavity as Determined by Acoustic Rhinometry, Department of Surgery, Section of Otolaryngology—Head and Neck Surgery University of Chicago, IL, USA, Nov. 1999, Abstract only.

Kjærgaard et al, The Assessment of Irritation Using Clinical Methods and Questionnaires, AIHAJ 62:711-716, Nov./Dec. 2001.

Klimek et al, Assessment of Rhinological Parameters for Evaluating the Effects of Airborne Irritants to the Nasal Epithelium, Centre for Rhinology and Allergology, Wiesbaden, Germany, Ludger. Klimek@t-online.de; PMID: 11981667 [PubMed—indexed for MEDLINE], Jun. 2002, Abstract only.

Lenders et al., Diagnostic Value of Acoustic Rhinometry: Patients With Allergic and Vasomotor Rhinitis Compared With Normal Controls, Dept. of O.R.L., University Hospital Ulm, Fed. Rep. of Germany; PMID: 2336526 [PubMed—indexed for MEDLINE], Mar. 1990, Abstract only.

Maeda et al., Increased Nasal Patency Caused by Smoking and Contraction of Isolated Human Nasal Mucosa, Department of Otolaryngology—Head and Neck Surgery, Toshiba Hospital, rhinology-tky@umin.ac.jp, PubMed, Jun. 2004, Abstract only.

Malm et al., Guidelines for Nasal Provocations With Aspects on Nasal Patency, Airflow, and Airflow Resistance, International Committee on Objective Assessment of the Nasal Airways, International Rhinologic Society; Department of Otorhinolaryngology, University Hospital, Malmo, Sweden, Lars.Malm@oron.mas.lu.se; PMID: 10780040 [PubMed—indexed for MEDLINE], Mar. 2000, Abstract only.

Marques et al., Pre- and Postoperative Evaluation by Acoustic Rhinometry of Children Submitted to Adenoidectomy or Adenotonsillectomy, Faculty of Medicine of Ribeirao Preto, University of Sao Paulo, Sao Paulo, Brazil; PMID: 15129941 [PubMed—indexed for MEDLINE], Mar. 2004, Abstract only.

Naito et al., Comparison of Perceptional Nasal Obstruction With Rhinomanometric and Acoustic Rhinometric Assessment, Department of Otolaryngology, Fujita Health University, School of Medicine, Kutsukake Toyoake, Aichi, Japan; knaito@fujita-hu.ac.jp; PMID: 11829185 [PubMed—indexed for MEDLINE], Dec. 2001, Abstract only.

Norback et al., Biomarkers and Chemosensory Irritations, Department of Medical Sciences/Occupational and Environmental Medicine, Uppsala University, University Hospital, 751 85 Uppsala, Sweden; dan.norback@medsci.uu.se; PMID: 11981668 [PubMed—indexed for MEDLINE], Jun. 2002, Abstract only.

Numminen et al., Comparison of Rhinometric Measurements Methods in Intranasal Pathology, Department of Otorhinolaryngology, Head and Neck Surgergy, Tampere University Hospital, Tampere, Finland; jura.numminen@pshp.fi; PMID: 12868368 [PubMed—indexed for MEDLINE] , Jun. 2003, Abstract only.

Ohkawa et al., Histamine H1 Receptor and Reactivity of the Nasal Mucosa in Sensitized Guinea Pigs, Department of Otorhinolaryngology, Mie University School of Medicine, Tsu, Japan; PMID: 10419037 [PubMed—indexed for MEDLINE] , Jun. 1991, Abstract only.

Ozturk et al., Effect of Intranasal Triamcinolone Acetonide on Bronchial Hyper-Responsiveness in Children With Seasonal Allergic Rhinitis and Comparison of Perceptional Nasal Obstruction With Acoustic Rhinometric Assessment, Department of Pediatrics, Division of Pediatric Allergy and Asthma, Gazi University Faculty of Medicine, Ankara, Turkey; PMID: 15236886 [PubMed—indexed for MEDLINE], Aug. 2004, Abstract only.

Pan et al., A Chamber-Experiment Investigation of the Interaction Between Perceptions of Noise and Odor in Humans, Department of Environmental and Occupational Medicine, University of Aarhus, Vennelyst Boulevard 6, 8000 Aarhus, Denmark; pan@mil.au.dk; PMID: 14586588 [PubMed—indexed for MEDLINE], Oct. 2003, Abstract only.

Parvez et al., Novel Techniques, Standardization Tools to Enhance Reliability of Acoustic Rhinometry Measurements, Procter & Gamble Health Care Research and Development Laboratory, Thane, India; PMID: 11225285 [PubMed—indexed for MEDLINE], Dec. 2000, Abstract only.

Parvez et al., Nasal Histamine Challenge: A Reproducible Model of Induced Congestion Measured by Acoustic Rhinometry, Procter & Gamble Health Care Research and Development Laboratory, Thane, India; PMID: 11225289 [PubMed—indexed for MEDLINE] , Dec. 2000, Abstract only.

Passali et al., Monitoring Methods of Nasal Pathology, ENT Department, University of Siena, Medical School, Italy; PMID: 10577805 [PubMed—indexed for MEDLINE], Oct. 1999, Abstract only.

Passali et al., Treatment of Hypertrophy of the Inferior Turbinate: Long-Term Results in 382 Patients Randomly Assigned to Therapy, Department of Otorhinolaryngology, University of Sienna Medical School, Italy, Jun. 1999, Abstract only.

Passali et al., Alterations in Rhinosinusal Homeostasis in a Sportive Population: Our Experience With 106 Athletes, Department of Otorhinolaryngology, University of Sienna Medical School, Sienna, Italy; passali@unisi.it, Oct. 2004, Abstract only.

Phipatanakul et al., The Efficacy of Montelukast in the Treatment of Cat Allergen-Induced Asthma in Children, Department of Pediatrics, Division of Allergy and Immunology, Children's Hospital, Harvard Medical School, Boston, Mass 02115, USA; PMID: 11994702 [PubMed—indexed for MEDLINE], May 2002, Abstract only.

Ragab et al., An Open Audit of Montelukast, A Leukotriene Receptor Antagonist, in Nasal Polyposis Associated With Asthma, Royal National Throat, Nose and Ear Hospital, London, UK; PMID: 11591188 [PubMed—indexed for MEDLINE], Sep. 2001, Abstract only.

Rasmussen et al., Particle Deposition in the Nose Related to Nasal Cavity Geometry, Department of Environmental and Occupational Medicine, University of Aarhus, Dennmark; PMID: 11072654 [PubMed—indexed for MEDLINE], Sep. 2000, Abstract only.

Rozsasi et al., Nasal Conditioning in Perennial Allergic Rhinitis After Nasal Allergen Challenge, Department of Otorhinolaryngology, University of Ulm, Ulm, Germany; ajnirozsasi@hotmail.com; PMID: 15248856 [PubMed—indexed for MEDLINE], Jul. 2004, Abstract only.

Sheahan et al., Induction of Nasal Hyper-Responsiveness by Allergen Challenge in Allergic Rhinitis: The Role of Afferent and Efferent Nerves, Department of Otolaryngology, Royal College of Surgeons in Ireland, Dublin, Ireland; rcostello@rcsi.ie; PMID: 15649265 [PubMed—indexed for MEDLINE], Jan. 2005, Abstract only.

Silkoff et al., Nasal Nitric Oxide Does Not Control Basal Nasal Patency or Acute Congestion Following Allergen Challenge in Allergic Rhinitis, Department of Medicine, Faculty of Medicine, University of Toronto, Ontario, Canada, Apr. 1999, Abstract only.

Takeno et al., Laser Surgery of the Inferior Turbinate for Allergic Rhinitis With Seasonal Exacerbation: An Acoustic Rhinometry Study, Department of Otolaryngology, Hiroshima University School of Medicine, Hiroshima, Japan; PMID: 12784987 [PubMed—indexed for MEDLINE], May 2003, Abstract only.

Taverner et al., Evaluation of the Dose-Response Relationship for Intra-Nasal Oxymetazoline Hydrochloride in Normal Adults, Department of Clinical and Experimental Pharmacology, University of Adelaide, South Australia, 5005 Australia; dtaverne@medicine.adelaide.edu.au; PMID: 10501820 [PubMed—indexed for MEDLINE], Sep. 1999, Abstract only.

Taverner et al., Validation by Fluid Volume of Acoustic Rhinometry Before and After Decongestant in Normal Subjects, Department of Clinical and Experimental Pharmacology, University of Adelaide, Adelaide, South Australia, 5005 Australia; dtaverne@medicine.adelaide.edu.au; PMID: 12357713 [PubMed—indexed for MEDLINE], Sep. 2002, Abstract only.

Taylor-Clark et al., Histamine Receptors That Influence Blockage of the Normal Human Nasal Airway, Department of Pharmacology, University College London, Gower Street, London WC1E6BT; PMID: 15685206 [PubMed—indexed for MEDLINE], Mar. 2005, Abstract only.

Turner et al., Role of Kinins in Seasonal Allergic Rhinitis: Icatibant, A Bradykinin B2 Receptor Antagonist, Abolishes the Hyper-responsiveness and Nasal Eosinophilia Induced by Antigen, Department of Pharmacology, University College of London, London, United Kingdom; PMID: 11149999 [PubMed—indexed for MEDLINE], Jan. 2001, Abstract only.

Valero, et al., Nasal and Bronchial Response to Exercise in Patients With Asthma and Rhinitis: The Role of Nitric Oxide, Unidad de Alegria, Servicio de Neumologia y Alerdia Respiratoria, Hospital Clinic, Universitat de Barcelona, Barcelona, Spain, Sep. 2005, Abstract only.

Walinder et al., Nasal Patency and Lavage Biomarkers in Relation to Settled Dust and Cleaning Routines in School, Department of Medical Sciences, Occupational and Environmental Medicine, Uppsala University Hospital, Sweden; robert.walinder@occmed.uu.se; PMID: 10360469 [PubMed—indexed for MEDLINE], Apr. 1999, Abstract only.

Walinder et al., Acoustic Rhinometry in Epidemiological Studies—Nasal Reactions in Swedish Schools, Department of Medical Sciences/Occupational and Environmental Medicine, University of Uppsala, Sweden; robert.walinder@medsci.uu.se; PMID: 11225291 [PubMec—indexed for MEDLINE], Dec. 2000, Abstract only.

Wang et al., Acoustic Rhinometry in Nasal Allergen Challenge Study: Which Dimensional Measures Are Meaningful?, Department of Otolaryngology, Faculty of Medicine, The National University of Singapore, Singapore; entwdy@nus.edu.sg; PMID: 15248855 [PubMed—indexed for MEDLINE], Jul. 2004, Abstract only.

Wilson et al., Evaluation of the Importance of Head and Probe Stabilisation in Acoustic Rhinometry, Asthma & Allergy Research Group, Department of Clinical Pharmacology & Therapeutics, University of Dundee, Scotland, UK; PMID: 11486446 [PubMed—indexed for MEDLINE], Jun. 2001, Abstract only.

Yamagiwa et al., Evaluation of the Effect of Localized Skin Cooling on Nasal Airway Volume by Acoustic Rhinometry, Institute of Environmental and Occupational Medicine, University of Arhus, Denmark; PMID: 2327639 [PubMed—indexed for MEDLINE], Apr. 1990, Abstract only.

* cited by examiner

SYSTEM AND METHOD FOR THREE-DIMENSIONAL AIRWAY RECONSTRUCTION, ASSESSMENT AND ANALYSIS

BACKGROUND OF THE INVENTION

The invention relates to a system and method for three-dimensional airway reconstruction, assessment and analysis. Specifically, the invention relates to a system and method for acquiring one- and two-dimensional data regarding a cavity, such as an esophagus or an airway, and manipulating that data to reconstruct a three-dimensional geometrical object representing that cavity. Suitable data collection methods include, but are not limited to, non-ionizing, non-invasive protocols including acoustic reflectometry, such as that performed by a DOS®- or Windows®-based pharyngometer or rhinometer. The resulting three-dimensional geometric object of the subject cavity can be used for diagnostics assessments, such as cavity constriction/obstruction, and therefore aid in the management and treatment of the constriction/obstruction, evaluate the efficacy of management and treatment of the constriction/obstruction and also provide information for use in outcome analysis, as well as forensic and medico-legal evaluations of diagnosis and treatment of cavity constriction/obstruction.

1. Field of the Invention

Obstruction/constriction of certain body cavities, such as airway passages, can create serious health problems. For example, sleep apnea is a debilitating and life-threatening condition that affects people worldwide. Sleep apnea occurs when tissues in the upper airway block the breathing passages. Obstructive sleep apnea is the most common type of sleep apnea. Normally, the muscles in the upper part of the throat allow air to flow into the lungs. When a person with obstructive sleep apnea falls asleep, these muscles are not able to keep the air passage open all the time. When the airway closes, breathing stops, oxygen levels fall and sleep is disrupted in order to open the airway. The disruption of sleep usually lasts only a few seconds. These brief arousals disrupt continuous sleep and prevent obstructive sleep apnea sufferers from reaching the deep stages of slumber, such as rapid eye movement (REM) sleep, which the body needs in order to rest and replenish its strength. Once breathing is restored, obstructive sleep apnea sufferers fall asleep only to repeat the cycle throughout the night.

Sleep apnea is suffered by adults and children alike. Sleep apnea can cause the sufferer to be sleepy throughout the day and is associated with cardiovascular disorders, including hypertension, coronary artery disease, heart failure, cardiac arrhythmia, stroke and metabolic abnormalities. Sleep apnea can be treated today by both surgical and non-surgical approaches. For example, by use of Continuous Positive Airflow Pressure ("CPAP"), the sufferer wears a mask that supplies a steady stream of air during sleep, where the airflow keeps the nasal passages open sufficiently to prevent airway collapse and apnea. Weight loss, change of sleep habits, behavior modification and wearing of oral appliances during sleep can also promote normal sleep.

In addition, people suffer from airway obstructions or constriction/narrowing (stenosis) due to congenital conditions and/or accidents.

In each case, evaluation of a cavity such as an airway is a valuable tool in analyzing a problem, and then developing a management and/or treatment plan for the sufferer of the problem. Also, evaluation of a cavity such as an airway is useful in providing information on outcome analysis for management and/or treatment plans for both care providers and insurance providers. Additionally, evaluation of the cavity has forensic and medico-legal uses.

2. Description of Related Art

Methods for acquiring data regarding the anatomy of body cavities and organs are known. For example, techniques such as radiographs (x-rays), including lateral cephalographs; CT scans, including cone-beam tomography, and nuclear MRI are often used to image body organs and cavities for evaluation and diagnostic purposes. These techniques have limited uses, however. Radiographs, including cephalographs, and CT scans expose the patient to potentially harmful ionizing radiation requiring appropriate precautions. Also, certain patient groups such as pregnant women might be excluded from such protocols. Also, certain techniques such as CT scans and nuclear MRI require post-processing of data to isolate certain cavities, such as the airway, because all tissues, including skin, muscle, bone, etc., are imaged simultaneously. Other techniques, such as cone-beam tomography, generate huge file sizes, which may exceed the resources available at a typical care-provider's office. Additionally, these techniques tend to be expensive, time-consuming and often require specially trained personnel.

Acoustic reflectometry is a non-invasive, non-ionizing protocol that produces a "one-dimensional" curve of the distance into the airway versus a two-dimensional cross-sectional area map of the upper airway. For example, U.S. Pat. No. 5,316,002, issued to Jackson et al. entitled "Nasopharyngealometric Apparatus and Method," the disclosure of which is incorporated by reference, discloses an apparatus and method for: determining the profile of the nasopharyngeal cavity by introducing acoustic signals into the nasal cavities of a subject; detecting the acoustic signals and acoustic reflections; generating electrical signals proportional to the amplitude of the acoustic signals and acoustic reflections; determining the length of the nasal septum separating the nasal cavities, and computing the value of the area-distance function of the nasopharyngeal cavity from the electrical signals and the length of the nasal septum. U.S. Pat. No. 5,823,965, issued to Rasmussen entitled "Device for Reflectometric Examination and Measurement of Cavities," the disclosure of which is incorporated by reference, also discloses an apparatus and method for reflectometric examination and measurement of human and animal cavities such as air and food passages. U.S. Pat. Nos. 5,746,699 and 5,666,960, both issued to Fredberg et al. and both entitled "Acoustic Imaging", the disclosures of which are incorporated by reference, disclose an apparatus for providing an output signal characteristic of the morphology of the respiratory tract. A transducer launches acoustical energy toward the opening of the tract, producing an incident wave and a reflected wave to form a transient wave-field representative of the morphology of the tract. In each of these disclosures, the result is a "two-dimensional" measurement of the cross-sectional area of the measured cavity as a function of a "one-dimensional" distance into the cavity.

Practitioners have used acoustical reflectometry to assess preoperative and postoperative nasal septal surgery; see LARRY SHEMEN, M.D., F.R.C.S., F.A.C.S. and RICHARD HAMBURG, M.D., F.A.C.S., "PREOPERATIVE AND POSTOPERATIVE NASAL SEPTAL SURGERY ASSESSMENT WITH ACOUSTIC RHINOMETRY," presented at the Annual Meeting of the American Academy of Otolaryngology-Head and Neck Surgery, Washington, D.C., September 29-Oct. 2, 1996, p. 338. The authors reported that the acoustic rhinometer allows objective measurement of nasal cavity volume, which is crucial in the diagnosis of nasal dysfunction. Such objective measurement allows for planning of appropriate treatment and evaluation of results after medical or surgical treatment. The authors also noted that objective documentation of nasal obstruction before and after surgery is being demanded by third-party payers, and allows for comparison of alternative procedures.

Other practitioners have noted that acoustic reflectometry can detect within seconds, and without the use of capnography, characteristic, distinctive and specific area-length profiles for both endotracheal and esophageal intubation. See DAVID T. RAPHEAL, M.D., Ph.D., "ACOUSTIC REFLECTOMETRY PROFILES OF ENDOTRACHEAL AND ESOPHAGEAL INTUBATION," Anesthesiology. 92(5): 1293-1299, May 2000.

Certain practitioners have reported on the size and pressure/area relationship of the pharynx as important factors in the pathogenesis of obstructive sleep apnea. See BRIGADIER GENERAL IBRAHIM KAMAL, M.D., "NORMAL STANDARD CURVE FOR ACOUSTIC PHARYNGOMETRY," available from the ENT Department, Police Authority Hospital, 26 Makram Oubaid Street, Nasr City, Egypt. Dr. Kamal reported that assessment of the upper airway for possible site(s) of obstruction/constriction is one of the keys to successful management of the condition, and that acoustic pharyngometry has the potential for localizing such sites. Dr. Kamal further reported that the acoustic pharyngometry technique is easy, rapid and cost-effective.

Acoustic reflectometry has also been used in connection with detection of conditions of the middle ear. For example, U.S. Pat. Nos. 5,868,682 and 5,699,809, both issued to Combs et al. and both entitled "Device and Process for Generating and Measuring the Shape of an Acoustic Reflectance Curve of an Ear", the disclosures of which are incorporated by reference, disclose a device and process for analysis of acoustic reflectance of components of an ear. The results can assist in diagnosis of an ear pathology such as abnormal pressure, presence of fluid in the middle ear or conductive hearing loss.

SUMMARY OF THE INVENTION

The invention relates to a system and method for three-dimensional airway reconstruction, assessment and analysis. The inventive system and method can be performed using data input captured, stored and exported using a DOS® or Windows®-based pharyngometer or rhinometer. A three-dimensional geometric object of the airway can be generated from the data input, in contrast to the "one-dimensional" curve of the cross-sectional area of the measured airway as a function of distance into the airway that is output from a pharyngometer or rhinometer. This computer-generated three-dimensional object can be presented graphically, and allows care providers to make assessments and comparisons for diagnostic or treatment purposes. The resulting three-dimensional geometric object can also be used for objective documentation of nasal obstruction before and after surgery as demanded by third-party payers, or can be used for forensic or medico-legal purposes.

The inventive system and method is fast, easy to use, does not require specialized training for the operator and can run on personal computers and laptops as may be found in a care provider's office. In addition, acoustic reflectometry is a non-ionizing, non-invasive protocol that can safely be used without the precautions, disadvantages and post-processing of previously known imaging methods, such as radiographs, including cephalographs, CT scans, including cone-beam tomography and MRI scans.

The resulting geometric object of the airway can be superimposed on a two-dimensional digital radiograph or digital photograph. This functionality permits the user to visualize a more anatomically-correct three-dimensional airway, and may provide the user with further information on site-specific airway obstruction/constriction e.g., before and after treatment, with or without an oral appliance etc.

It is therefore an object of the invention to provide a system and method to create a reconstructed three-dimensional geometric object representing a cavity, such as an airway, using one- and two-dimensional input data, such as cross-sectional area of an airway measured as a function of distance from the opening of the airway cavity.

It is another object of the invention to provide a system and method to create a reconstructed three-dimensional geometric object representing a cavity, such as an airway, using one- and two-dimensional input data including cross-sectional area of an airway measured as a function of distance from the opening of the airway cavity using non-ionizing, non-invasive protocols, such as acoustic reflectometry.

It is another object of the invention to provide a system and method to create a reconstructed three-dimensional geometric object representing a cavity, such as an airway, using one- and two-dimensional input data including cross-sectional area of an airway measured as a function of distance from the opening of the airway cavity using acoustic reflectometry.

It is yet another object of the invention to provide a system and method to create a reconstructed three-dimensional geometric object representing a cavity, such as an airway, using one- and two-dimensional input data including cross-sectional area of an airway measured as a function of distance from the opening of the airway cavity using acoustic reflectometry techniques including a Pharyngometer™ or rhinometer.

It is yet another object of the invention to superimpose a reconstructed three-dimensional geometric object representing a cavity, such as an airway, created using one- and two-dimensional input data including cross-sectional area of an airway as measured as a function of distance from the opening of the airway cavity onto a two dimensional digital radiograph or digital photograph of that cavity.

It is yet another object of the invention to provide a process and system for digital manipulation of a reconstructed three-dimensional geometric object representing a cavity, such as an airway, created using one- and two-dimensional input data including cross-sectional area of an airway as measured as a function of distance from the opening of the airway cavity.

It is yet another object of the invention to provide a system and method for analyzing cavity characteristics, such as length, area and volume to identify and quantify airway obstructions/constrictions/narrowing (stenosis), using a reconstructed three-dimensional geometric object representing a cavity, such as an airway, created using one- and two-dimensional input data including cross-sectional area of an airway measured as a function of distance from the opening of the airway cavity.

It is yet another object of the invention to provide a system and method for assessing/evaluating treatment methods/protocols to manage and/or alleviate cavity dysfunction, such as airway obstructions, using a reconstructed three-dimensional geometric object representing a cavity, such as an airway, created using one- and two-dimensional input data including cross-sectional area of an airway measured as a function of distance from the opening of the airway cavity.

It is yet another object of the invention to provide a system and method for assessing/evaluating the efficacy of treatments of and/or management of cavity obstructions, such as airway obstructions, using a reconstructed three-dimensional geometric object representing a cavity, such as an airway, created using one- and two-dimensional input data including cross-sectional area of an airway measured as a function of distance from the opening of the airway cavity.

The system and method of the invention include a programmable processor for receiving one- and two-dimensional data representing cross-sectional area and distance of a cavity, such as an airway, measured from the opening of the cavity; calculating a plurality of circles, which represent the cross-sectional area of the cavity at known distances from the starting point (the opening of the cavity) and from each other (adjacent circular cross-sectional areas) from the input data; forming a triangular mesh from the plurality of circles that represent the cross-sectional area of the cavity; and creating output data including a three-dimensional geometric object comprising the triangular mesh representative of the cavity enclosed by a rendered surface, along with other data representing length, area and volume parameters of the cavity. The three-dimensional geometric object can be manipulated to evaluate and compare the management and/or treatment of any conditions of the cavity, such as obstruction of an airway. Further, different three-dimensional geometric objects can be compared to evaluate pre- and post-treatment efficacy due to management and/or treatment of the cavity, such as an obstruction of an airway. Additionally, the three-dimensional geometric object can be superimposed on a digital radiograph or digital photograph of the cavity to permit the user to visualize a more anatomically-correct three-dimensional airway, and provide the user with further information on site-specific airway obstruction/constriction.

Further, different three-dimensional geometric objects can be manipulated to compute an averaged or mean cavity, such as an average airway. Furthermore, these averaged or mean objects can be compared for diagnostic or treatment planning purposes.

Yet further, groups of different three-dimensional geometric objects can be represented and plotted in statistical space, so that a new, three-dimensional geometric object can be compared to evaluate the chances of that new object being in the same group or a different group with respect to the three-dimensional geometric objects plotted.

These and other features of various embodiments will become readily apparent to those skilled in the art upon review of the detailed description that follows.

DETAILED DESCRIPTION OF PREFERRED EMBODIMENTS

For the purposes of promoting an understanding of the embodiments described herein, reference will be made to preferred embodiments and specific language will be used to describe the same. The terminology used herein is for the purpose of describing particular embodiments only, and is not intended to limit the scope of the present invention. As used throughout this disclosure, the singular forms "a," "an," and "the" include plural reference unless the context clearly dictates otherwise. Thus, for example, a reference to "a composition" includes a plurality of such compositions, as well as a single composition, and a reference to "a geometric object" is a reference to one or more geometric objects and equivalents thereof known to those skilled in the art, and so forth.

Figure 1:
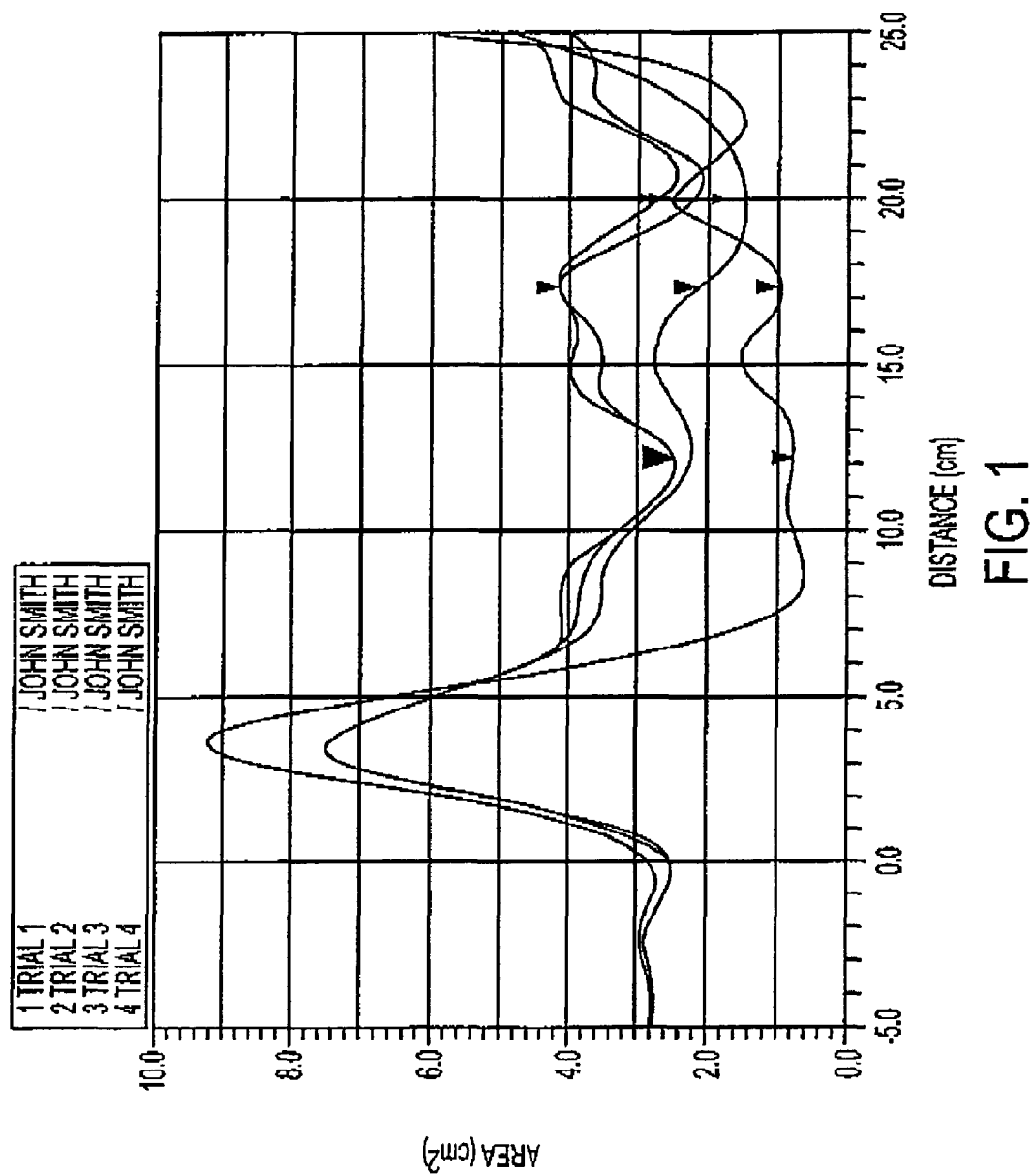
FIG. 1 is a graph depicting a one-dimensional curve obtainable from an acoustic reflectometry device, such as a Pharyngometer™ or rhinometer, and showing the cross-sectional area of a measured airway as a function of distance from the opening of the airway.

Acoustic reflectometry provides one- and two-dimensional information on a cavity. For example, the Eccovision Acoustic Pharyngometer® and/or Eccovision Acoustic Rhinometer® manufactured by Hood Laboratories, located in Pembroke, Massachusetts and distributed by Sleep Group Solutions LLC of Miami, Florida, are non-invasive, non-ionizing protocols that can determine the dimensions of the oral airway past the epiglottis or the nasal cavity. Details on the operation of the Eccovision Acoustic Pharyngometer® and/or Eccovision Acoustic Rhinometerg® are available from Hood Laboratories, and are hereby incorporated by reference. The output of the Eccovision Acoustic Pharyngometer® and/or Eccovision Acoustic Rhinometer® is a one-dimensional graph/curve providing information on the cross-sectional area of the oral airway past the epiglottis or nasal cavity as a function of the distance into the oral airway past the epiglottis or nasal cavity. FIG. 1 depicts a typical output for a Eccovision Acoustic Pharyngometer™ and an Eccovision Acoustic Rhinometer™.

The system and method of the invention processes the data acquired from the Eccovision Acoustic Pharyngometer® and/or Eccovision Acoustic Rhinometer® to create a three-dimensional geometric object depicting the oral airway past the epiglottis or the nasal cavity. The output of the Eccovision Acoustic Pharyngometer® and/or Eccovision Acoustic Rhinometer® are files containing a sequence of distances (d0, d1, . . . , dn–1) and the corresponding cross-sectional areas (A0, A1, . . . An–1) of the oral or nasal airway past the epiglottis or nasal cavity, respectively. A table depicting the typical file content from the Eccovision Acoustic Pharyngometer® and/or Eccovision Acoustic Rhinometer® is included in FIG. 2. A graph of these data provides a curve similar to that shown in FIG. 1.

Figure 3:
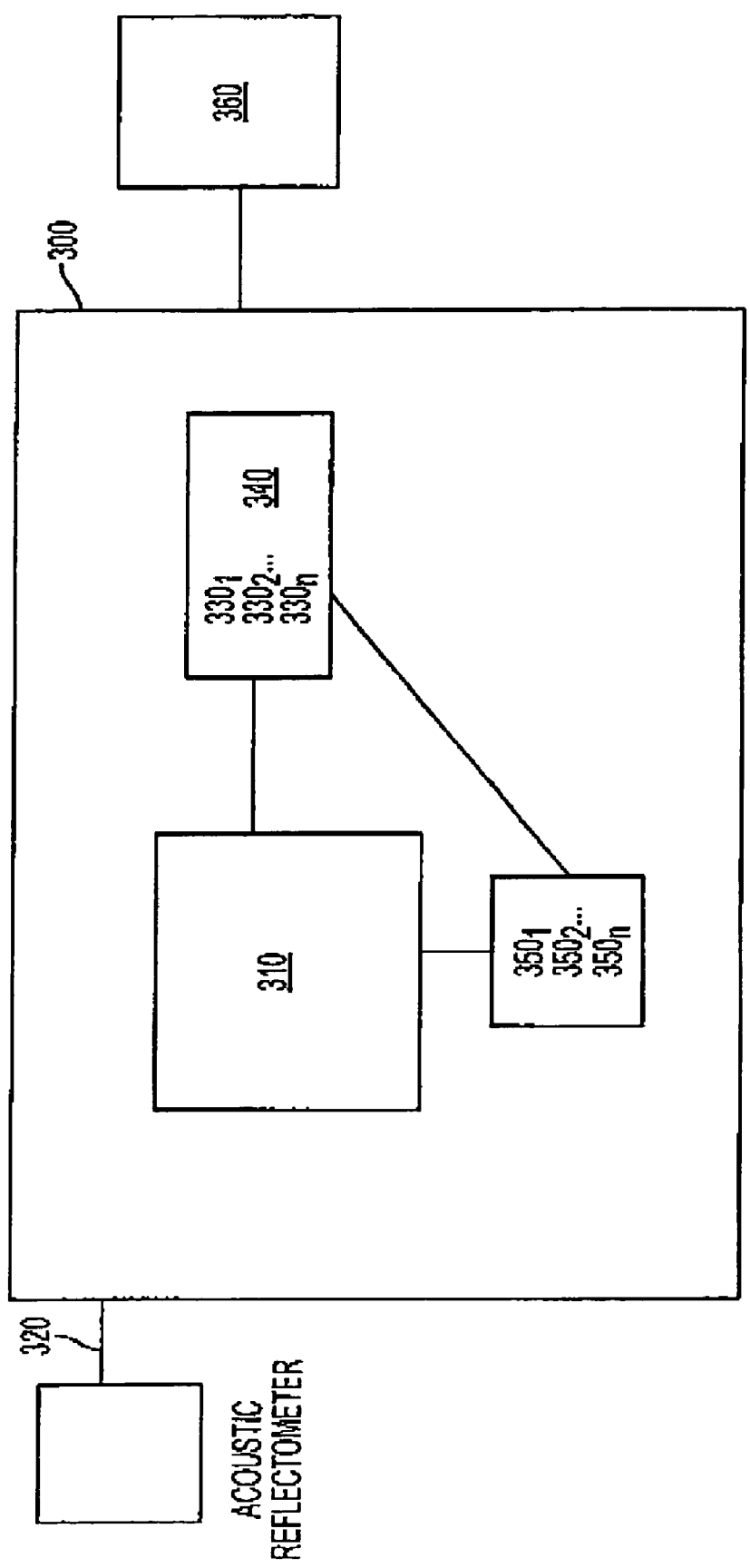
FIG. 3 is a schematic diagram of the system of the invention.

The system 300 of the invention is depicted in FIG. 3, and includes a processor 310 programmed to process data acquired from an Eccovision Acoustic Pharyngometer® and/or Eccovision Acoustic Rhinometer® from a cavity to be measured. Typically, data measured by the Eccovision Acoustic Pharyngometer® and/or Eccovision Acoustic Rhinometer® are captured, stored and saved in proprietary format, and then exported to the system of the invention 300 over link 320. The acquired data are then stored as simple ASCII or text files $330_i$ in a storage unit 340. The stored files $330_i$ are processed by the processor 310 according to programmed algorithms that encode a method for three-dimensional airway reconstruction, assessment and analysis. Alternatively, the acquired data can be processed directly by the processor 310 to provide a reconstructed three-dimensional airway or cavity. The system 300 can be installed on a personal computer or laptop.

The processor 310 checks the acquired data for format, including errors during data capture and consistency and modifies the data if necessary prior to storage in files $330_i$ in the data storage area 340. Alternatively, the acquired data can be checked for format prior to processing, if the acquired data are to be processed prior to storage in files $330_i$ in data storage area 340. For example, measurements associated with the acoustic reflectometer tube are discarded, as well as null pairs and repeated distances. Details on the operation of the Pharyngometer and Rhinometer are available and on how the data are initially processed are available from Hood Laboratories, and are hereby incorporated by reference. The data storage area 340 that is used to store the data that is acquired from the Eccovision Acoustic Pharyngometer® and/or Eccovision Acoustic Rhinometer® can include any storage now known or later developed, and can include a 3.5"floppy disk, ZIP disk, CD, USB-drive or mini hard-drive.

Figure 4:
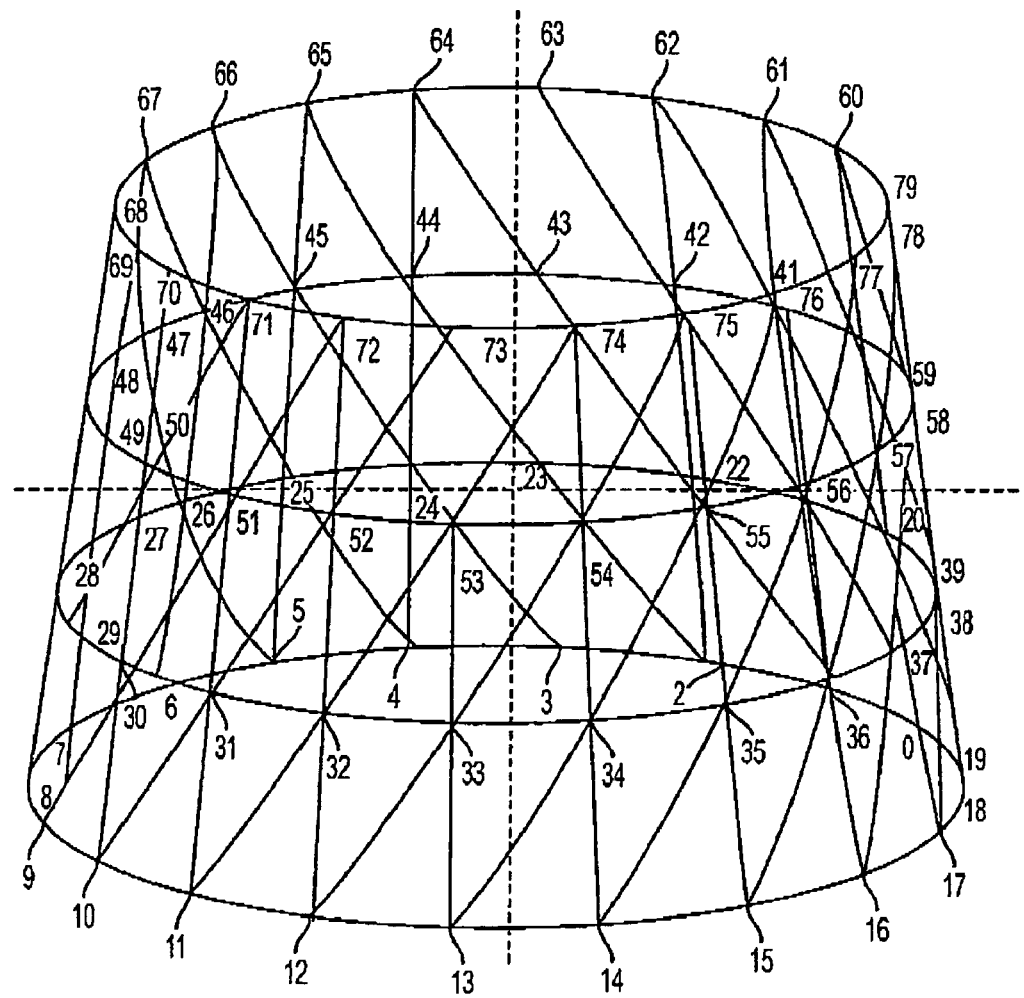
FIG. 4 is a graphic depicting a three-dimensional geometric object of a cavity, such as an airway, created using output data such as that shown in FIG. 2.

The processor 310 upon command retrieves a stored file $330_i$, and then processes the acquired data stored in file $330_i$ according to the method of the invention to create output data $350_i$ that can be graphed to form a three-dimensional geometric object representative of the cavity, along with other data representative of length, area and volume parameters of the cavity. FIG. 4 depicts typical graphical outputs of three-dimensional geometrical objects of a cavity created using one- and two-dimensional data acquired from an acoustic reflectometer, such as the Eccovision Acoustic Pharyngometer® and/or Eccovision Acoustic Rhinometer®. Alternatively, output data $350_i$ can be obtained by directly processing and graphing acquired data from the acoustic reflectometer, without first storing the acquired data in a file $330_i$ in data storage area 340. The output data $350_i$ can be stored in the data storage area 340 or exported if required or desired.

Figure 6:
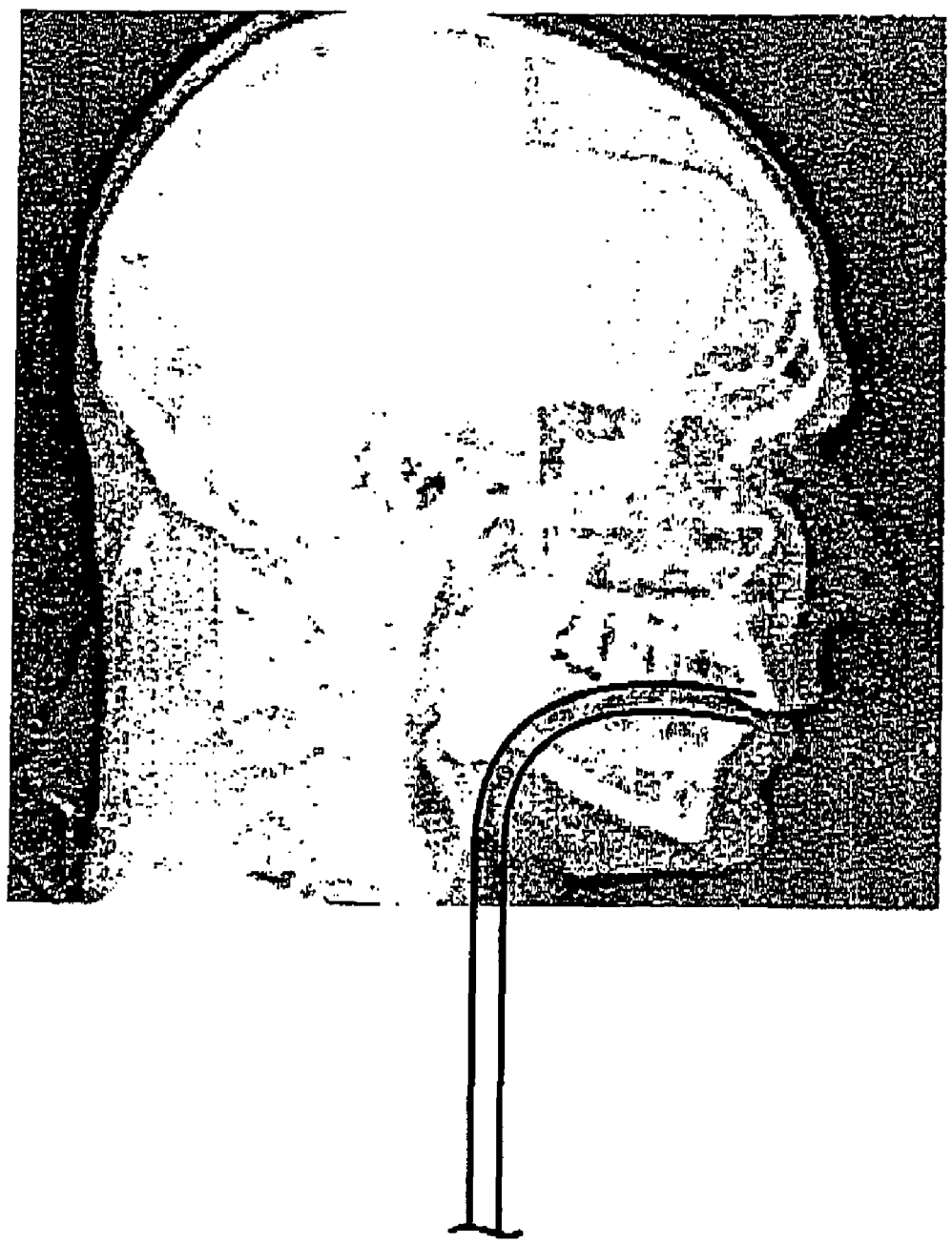
FIG. 6 is a depiction of a reconstructed three-dimensional geometric object of an airway superimposed on a digital radiograph of the corresponding patient, according to one embodiment of the invention.

The processor 310 is further programmed to retrieve and compare output data $350_i$ to other data, including standardized data or data relating to the same cavity but taken at different points in time, such as pre-treatment and post-treatment. Such comparison may be useful for diagnostic and treatment planning purposes, measuring efficacy of management and/or treatment of conditions of the cavity, such as obstructions/narrowing of the airway, for example to compare effectiveness of pre- and post-management and treatment of the cavity. The processor 310 can be further programmed to manipulate the stored output data $350_i$ to evaluate management and/or treatment of any conditions of the cavity, such as obstruction/narrowing of an airway. Additionally, the processor 310 can be programmed to superimpose the stored output data $350_i$ on a digital radiograph or digital photograph of the cavity to permit a user to visualize a more anatomically-correct 3-D airway, and provide the user with further information on site-specific airway obstruction/constriction, as seen in FIG. 6. A display unit 360 can be placed in communication with the processor 310 or with any system to which output data $350_i$ may be exported that can graphically display the output data $350_i$ as well as the manipulations of the output data $350_i$, using standard personal computer monitors and similar visual display units. Additionally, the output data $350_i$ can be exported or printed on various media using standard personal computer printers and peripherals. Alternatively, output data $350_i$ can be compared to other images, be displayed on display unit 360, or manipulated without first storing the output data $350_i$ in data storage area 340.

As known to those skilled in the art, the Eccovision Acoustic Pharyngometer® and/or Eccovision Acoustic Rhinometer® are operable using standard DOS® and Windows® operating systems installed on personal computers. The processors of those computer systems can easily perform the processing steps to manipulate the acquired data to provide the geometric objects depicting the cavity according to the invention, and the output data files $350_i$ are of a size that computer systems found in typical care-provider offices can easily store a plurality of such files.

Figure 5:
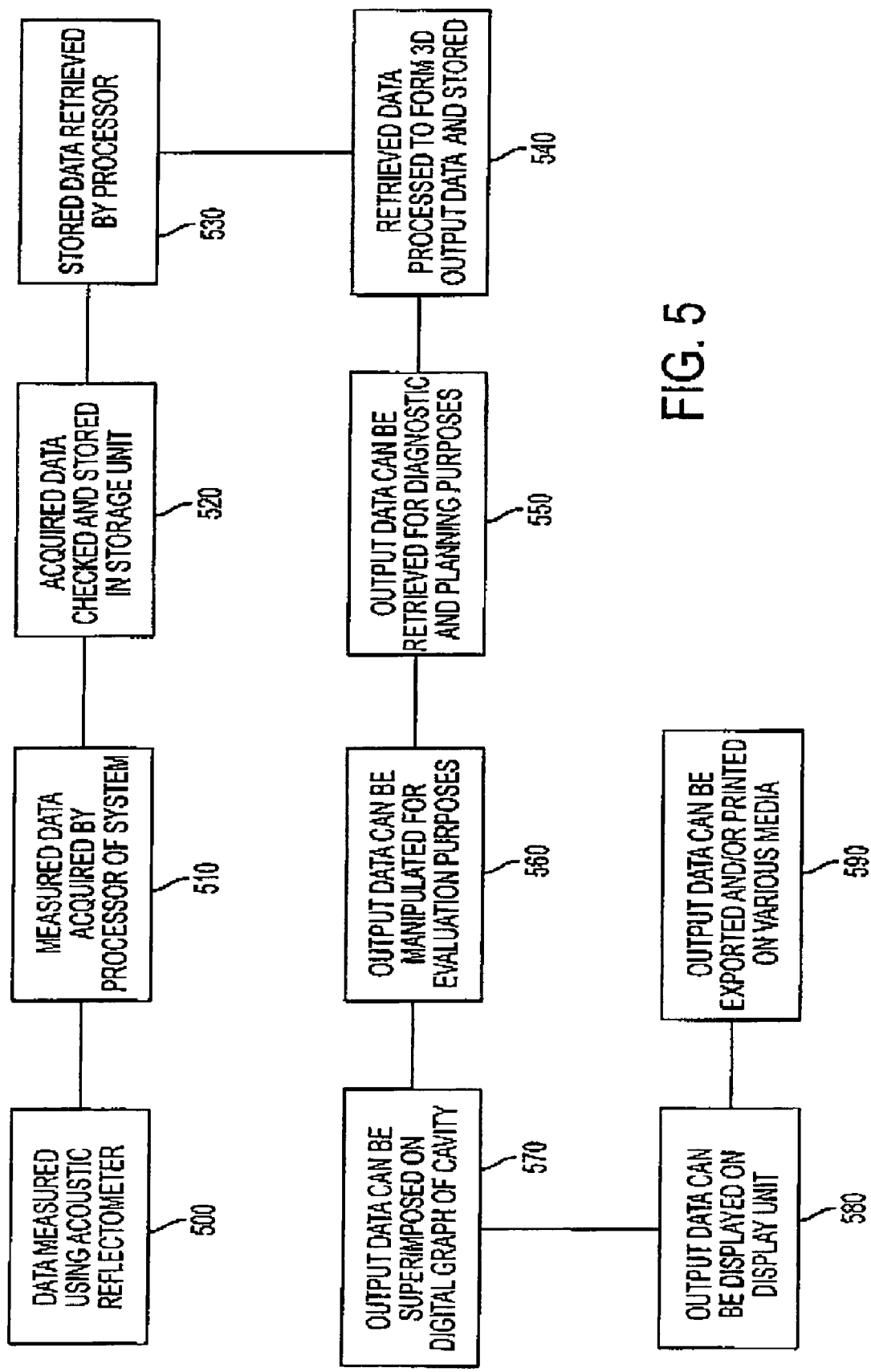
FIG. 5 is a flowchart depicting the steps performed in one embodiment of the method of the invention.

A flow scheme of the method of the invention is depicted in FIG. 5. At 500, data are measured using an acoustic reflectometer, such as an Eccovision Acoustic Pharyngometer® and/or Eccovision Acoustic Rhinometer®, from a cavity. The Eccovision Acoustic Pharyngometer®and/or Eccovision Acoustic Rhinometer® can be operated at standard operating conditions, as described in literature available from Hood Laboratories and as known to those skilled in the art. The measured data are acquired by the processor 310 of the system of the invention at 510. At 520, the acquired data are checked by the processor 310 for format, including errors during data capture and consistency, and stored in files $330_i$ in the storage unit 340 if the files are acceptable according to predetermined protocols and standards. The stored files $330_i$ are retrieved by the processor 310 at 530, and the data stored in the stored files $330_i$ are processed at 540 according to the method of the invention to create output data $350_i$ that can be graphed to form a three-dimensional geometric object representative of the cavity, along with other data representative of length, area and volume parameters of the cavity. FIG. 4 depicts typical graphical outputs of three-dimensional geometrical objects of a cavity created using one- and two-dimensional data acquired from an acoustic reflectometer, such as Eccovision Acoustic Pharyngometer® and/or Eccovision Acoustic Rhinometer®. In another embodiment, acquired data is processed by processor 310 at 540 directly prior to storage in files $330_i$. The output data $350_i$ can be stored at 540 in the data storage area 340 or exported if required or desired.

At 550, the processor 310 may retrieve and compare output data $350_i$ from a plurality of stored files $330_i$ for diagnostic and treatment planning purposes, measuring efficacy of management and/or treatment of conditions of the cavity, such as obstructions/narrowing of the airway, for example to compare effectiveness of pre- and post-management and treatment of the cavity. At 560, the processor 310 can further manipulate the stored output data $350_i$ to evaluate management and/or treatment of any conditions of the cavity, such as obstruction/narrowing of an airway. At 570, the processor 330 can superimpose the stored output data $350_i$ on a digital radiograph or digital photograph of the cavity to permit a user to visualize a more anatomically-correct three-dimensional airway, and provide the user with further information on site-specific airway obstruction/constriction. At 580, the output data $350_i$ can be graphically displayed on display unit 360 as well as the manipulations of the output data $350_i$. At 590, the output data $350_i$ can be exported or printed on various media using standard personal computer printers and peripherals. Any of steps 550 through 590 can be performed individually or in combination with any other step, or may be performed in any order desired by the user of the system and method of the invention. In one embodiment, output data $350_i$ are not stored in data storage area 340 as shown in 550 and then retrieved prior to comparison, manipulation and/or superimposition, but rather output data $350_i$ can be used for comparison, manipulation and/or superimposition purposes and applications substantially directly after processing of the acquired data by processor 310.

Figure 2:
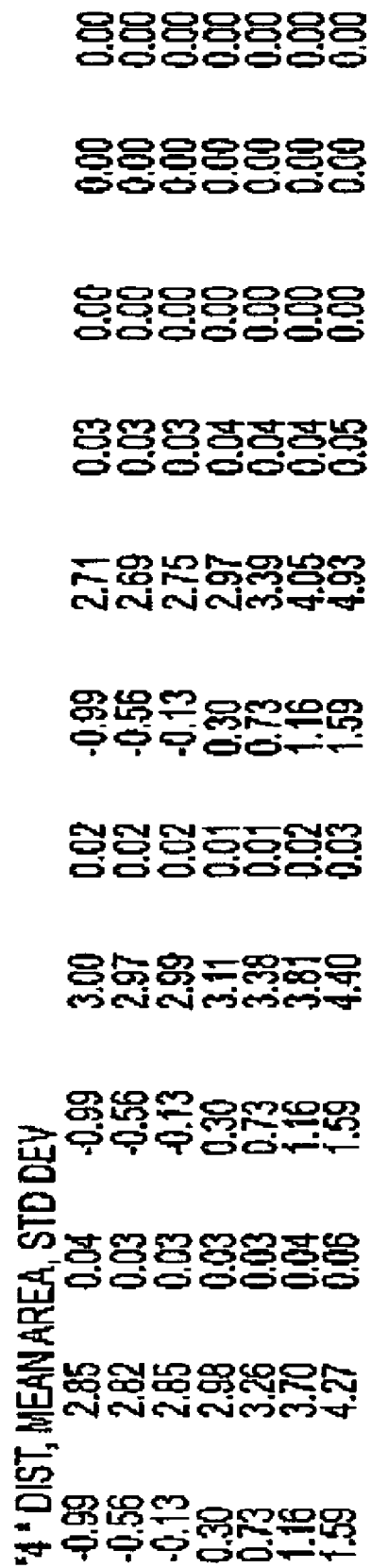
FIG. 2 is a table showing typical output data of an acoustic reflectometry device, such as a Pharyngometer™ or rhinometer.

The method of the invention uses programmed algorithms that encode a method for three-dimensional airway reconstruction, assessment and analysis. The method begins using data acquired from an acoustic reflectometer, which data comprise n data points, including distance and corresponding cross-sectional area as shown in FIG. 2. A plurality of circles, each having a plurality of nodes, are generated from the acquired data as follows.

Each circle represents the corresponding cross-sectional area at a known distance as recorded and captured using an acoustic reflectometer, such as an Eccovision Acoustic Pharyngometer® and/or Eccovision Acoustic Rhinometer®. The number of nodes and the number of circles are calculated when n two-dimensional points are acquired and a net three-dimensional surface is obtained having nl times nr nodes, where nl can be equal or not to n.

Each node represents homologous points on each circle. In one embodiment, the number of nodes per circle nr equals 40, but this can be changed according to the requirements of the user in order to increase or decrease resolution of the three-dimensional object that is generated. For example, a featureless (smooth) three-dimensional object indicates that default settings should be increased, while excessive resolution can result in a correspondingly large file size and default values may be decreased, if desired or if necessary. Those of ordinary skill in the art will be able to select other values of nr to provide desired results to provide a desired three-dimensional object and file size.

The number of circles, or nl, is then calculated by the formula:

$$nl=nr(dmax/2\pi rave)$$

where dmax and rave are calculated from the acquired data and comprise the maximum distance d from the origin of the cross-sectional area of a measured cavity area having radius $r[i]$, and rave comprises the average radius of the cross-sectional areas of the measured cavity area. When processing the acquired data, new radii can be interpolated according to the requirements of the user. Typically, nr will equal or exceed at least 3 and nl will equal or exceed at least 2, but there is no limit on the upper value limit of nr and nl. However, the value for nl is related to the data input from the acoustic reflectometer.

nl times nr nodes are then generated using the following formulae:

$$x[i][k]=D[i];$$

$$y[i][k]=R[i]*\cos(cita(k)); \text{ and}$$

$$z[i][k]=R[i]*\sin(cita(k)),$$

where $D[i]$ is the distance of the cross-sectional area from the origin, $cita(k)$ moves step by step from 0 to 180 degrees (nr steps), and i goes from 0 to (nl−1). The nodes obtained are then morphed, or bent, starting from three parameters: dPC1, dPC2 and dAngle. This process provides a more anatomically correct airway, since the default data input from the acoustic reflectometer provides a "straight tube." These parameters are selected according to the patient's anatomical features. For example, the data input from the acoustic reflectometer starts at the teeth or nostril. The user of the system and method of the invention can decide where to bend the "straight tube" by examining the corresponding patient's lateral cephalograph or by other measurements or techniques, knowing that certain features of the "straight tube" (for example, its narrowest part) are to be superimposed on the epiglottis of the corresponding patient's lateral cephalograph. During superimposition, the user has enough elements to morph the airway according to the corresponding patient's radiograph. dPC1 represents the site where bending will begin, dPC2 represents the site where bending will end and dAngle represents the angle at which the "straight tube" will be bent between these two sites.

The number of rotations performed in the morphing step are calculated as follows:

$$nl(dPC2-dPC1)/100=\#rotations,$$

where the first $[nl*(dPC1/100)]$ circles are not transformed. For example, where nl=100, dPC1=30%, dPC2=70% and dAngle=45°, 40 rotations would be executed, and the first 30 circles are not transformed. The resulting rotation is then distributed evenly per circle over the site to be bent such that bending is implemented by rotation of the circles located between dPC1 and dPC2. In this example, the following rotations are carried out:

| Rotation Number | Rotation angle | Circles simultaneously rotated |
| --- | --- | --- |
| 1 | 45°/40 = 1.125° | 31, 32, 33, 34, 35 . . . 99 |
| 2 | 45°/40 = 1.125° | 32, 33, 34, 35 . . . 99 |
| 3 | 45°/40 = 1.125° | 33, 34, 35 . . . 99 |
| . | . | . |
| . | . | . |
| . | . | . |
| 40 | 45°/40 = 1.125° | 70 . . . 99 |

In performing the rotations, in the first rotation the first circle as well as all of the following circles are rotated simultaneously. In the second rotation, the second circle as well as all of the following circles are rotated simultaneously, but the first circle (or, in the case of the third and later rotations, all circles before them) remain unchanged.

The plurality of nodes following the morphing step describes the three-dimensional form, or geometric object, of the cavity. The generated circles comprising the generated nodes are connected to form a triangular mesh, as shown in FIG. 4. The triangles are generated by standard triangulation routines known to those of ordinary skill in the art.

Once the triangles are generated from the acquired data and connected to create the final form as seen in FIG. 4, the final form can be bent or morphed, using a spline interpolation. The final form can be bent or morphed in the three planes of space to any angle between 0-360°. This process involves comparing homologous triangular finite elements as calculated from the acquired data using finite element analysis. FIG. 4 depicts a reconstructed three-dimensional object representing a portion of an airway, having eighty (80) nodes.

Finite element analysis consists of a computer model of a material or design that is stressed and analyzed for specific results. Finite element analysis can be used to modify an existing structure to analyze the structure under a new condition, and can be used to determine design modifications to meet the new condition. Finite element analysis uses a complex system of points called nodes which make a grid called a mesh, which mesh is programmed to contain the material and structural properties which define how the structure will react to certain loading conditions. Nodes are assigned at a certain density throughout the material depending on the anticipated stress levels of a particular area. Regions which will receive large amounts of stress usually have a higher node density than those which experience little or no stress.

In this case, the nodes are homologous landmarks evenly distributed throughout the form. The mesh acts like a spider web in that from each node, there extends a mesh element to each of the adjacent nodes. From these data, area factor, deformation factor and principal axes are calculated which are useful for detecting changes in size (e.g. length, area or volume), changes in shape (e.g. a sphere (soccer ball) changing into an ellipsoid (football) of the same volume), and the directionality in which those changes occurred (e.g. in the vertical, horizontal or transverse axes). The parameters to be taken into account during transformation of the final form include circumference diameter D; circumference area Ac; ellipse major axis S1; ellipse minor axis S2; ellipse area Ae; unit vector along S1 axis e1; and unit vector along S2 axis e2. From these values, the following factors can be calculated that are used to describe mathematically how the triangle was transformed:

| | |
|---|---|
| Area factor | $fA = Ae/Ac$ |
| Deformation factor | $fD = S1/S2$ |
| Principal axis direction | e1 |

Those of ordinary skill in the art of finite element analysis can calculate these parameters without undue experimentation.

The ability to transform the final form aids in evaluating management and/or treatment methods of conditions of the cavity. For example, management and/or treatment of sleep apnea may be aided by transforming the final form to determine the parameters of certain treatments, such as oral appliances or the settings for CPAP.

The final form as represented by the output data $350_i$ which is created by connecting the triangular mesh can be stored in the data storage unit 340. The output data $350_i$ includes data regarding lengths, areas and volumes of the cavity. The final form can also be displayed on a display unit 360, using surface rendering. While on the display unit 360, the final form output data $350_i$ can be superimposed on other three-dimensional data or on two-dimensional digital radiographs or digital photographs of the cavity. FIG. 6 depicts the superimposition of a final form of a reconstructed three-dimensional object representing an airway onto a digital radiograph of the corresponding patient's airway. This functionality permits the user to visualize a more anatomically-correct three-dimensional airway, and may provide the user with further information on site-specific airway obstruction/constriction e.g., before and after treatment, with or without an oral appliance, etc.

Stored forms can be compared to other stored forms, as well. For example, using finite-element analysis, a stored form of a normal subject can be compared with the stored form of a patient with sleep apnea, having the same number of nodes. Using a pseudocolor-coded scale, the user can evaluate the degree of severity of the condition, using finite-element analysis to localize and quantify the changes. As well, an average form can be computed for a population. For example, the average airway of adult males can be compared with the average airway of adult females. Similarly, the average airway of boys can be compared with the average airway of girls, etc.

The output data $350_i$ is useful for many purposes, including but not limited to analysis of airway obstructions/constrictions and analysis of management/treatment options; determination of efficacy of treatment of airway obstructions by comparison of pre- and port-treatment output data; objective measurement of efficacy of treatment for use by third parties, such as insurance carriers; and forensic and medicolegal applications.

It is possible to extend the inventive system and method to three-dimensional elements as well. Triangles are replaced by pyramids (tetrahedrons) with four landmarks as vertices. The circumference inside the triangle becomes a sphere inside the pyramid, which is transformed into an ellipsoid. Area factor is replaced by Volume factor, and two deformation factors and three parameters are required to define ellipsoid orientation. In this context, only Volume factor is considered for pyramids.

Frequently, three-dimensional forms are described by the enveloping surface, which is mathematically simulated by a mesh composed of a large number of triangular elements that are transformed simultaneously with the transformation. Area and deformation factors can also be obtained for these triangular elements.

Although the system and method was described in terms of data measured by an acoustic reflectometer of an airway cavity, the system and method is also suitable for other types of data and other cavity measurements where three-dimensional reconstruction and analysis would be desirable such as tracheal stenosis, either analog or digital. Other suitable modifications and adaptations of the variety of conditions and parameters normally encountered in therapy are within the spirit and scope of the invention.

What is claimed is:

1. A system comprising:
   a processor configured to receive
      cross-sectional data representative of cross-sectional areas of a cavity of an object being measured by an acoustic reflectometer at a plurality of distances from an origin point of the cavity, and
      feature data representative of at least a portion of the anatomical features of the object; and
   a storage unit configured to store a plurality of data files, the data files comprising the received cross-sectional data,
   wherein the processor is programmed to create a three-dimensional graphical representation of the cavity by calculating a plurality of nodes based on the cross-sectional data, forming a plurality of circles based on the calculated nodes, rotating the plurality of circles in accordance with the feature data, and connecting the nodes following rotation of the plurality of circles to form a triangular mesh, and
   the storage unit is configured to store the three-dimensional graphical representation.

2. The system of claim 1, further comprising a display unit to display the three-dimensional representation of the cavity.

3. The system of claim 1, wherein the object comprises a mammal.

4. The system of claim 3, wherein the object comprises a human being.

5. The system of claim 1, wherein the cavity comprises an airway.

6. The system of claim 1, wherein the acoustic reflectometer comprises one of a pharyngometer or a rhinometer.

7. The system of claim 1, wherein the processor is further programmed to manipulate the three-dimensional representation of the cavity to analyze the effect of a new condition of the cavity.

8. The system of claim 7, wherein the processor is further programmed to measure changes in size, changes in shape, and the directionality of changes to the cavity under a new condition.

9. The system of claim 1, wherein the processor is programmed to superimpose the three-dimensional representation of the cavity on a digital radiograph or digital photograph of the cavity.

* * * * *